(12) United States Patent
Ma et al.

(10) Patent No.: US 12,031,956 B2
(45) Date of Patent: Jul. 9, 2024

(54) SYSTEM AND METHOD OF MONITORING VIBRATION OF A BLASTING MODEL TEST FOR A JOINTED ROCK MASS

(71) Applicant: ANHUI UNIVERSITY OF SCIENCE AND TECHNOLOGY, Huainan (CN)

(72) Inventors: Qinyong Ma, Huainan (CN); Qingqing Su, Huainan (CN); Pu Yuan, Huainan (CN)

(73) Assignee: ANHUI UNIVERSITY OF SCIENCE AND TECHNOLOGY, Huainan (CN)

(*) Notice: Subject to any disclaimer, the term of this patent is extended or adjusted under 35 U.S.C. 154(b) by 401 days.

(21) Appl. No.: 17/524,696

(22) Filed: Nov. 11, 2021

(65) Prior Publication Data
US 2022/0244155 A1   Aug. 4, 2022

(30) Foreign Application Priority Data
Nov. 10, 2020 (CN) .......................... 202011249459.7

(51) Int. Cl.
*G01N 3/313* (2006.01)
*E21D 9/00* (2006.01)
(Continued)

(52) U.S. Cl.
CPC ............ *G01N 3/313* (2013.01); *E21D 9/003* (2013.01); *G01N 3/066* (2013.01); *G01N 3/068* (2013.01);
(Continued)

(58) Field of Classification Search
CPC .. G01N 3/313; G01N 33/24; G01N 2203/001; G01N 2203/003;
(Continued)

(56) References Cited

FOREIGN PATENT DOCUMENTS

CN   110108551 A * 8/2019 ............. G01N 29/14
CN   110108571 A * 8/2019 ............. G01M 5/005
(Continued)

OTHER PUBLICATIONS

Castro-Caicedo, Alvaro, María Julia Nieto-Callejas, and Pedro Torres. "Fiber Bragg grating strain sensor for hard rocks." 24th International Conference on Optical Fibre Sensors. vol. 9634. SPIE, 2015. (Year: 2015).*
Du G, Li Z, Song G. A PVDF-Based Sensor for Internal Stress Monitoring of a Concrete-Filled Steel Tubular (CFST) Column Subject to Impact Loads. Sensors (Basel). May 23, 2018;18(6):1682. doi: 10.3390/s18061682. PMID: 29882909; PMCID: PMC6021836. (Year: 2018).*
(Continued)

*Primary Examiner* — Son T Le
*Assistant Examiner* — Brian Butler Geiss
(74) *Attorney, Agent, or Firm* — Bochner PLLC; Andrew D. Bochner

(57) ABSTRACT

A system of monitoring vibration of a blasting model test for a jointed rock mass and a method are provided. The system includes: a loading subsystem for three-way load, a model-surface blasting-vibration acquisition subsystem, and a model-interior dynamic stress-strain acquisition subsystem. The system and the method are provided, and a blasting model for a transparent jointed rock mass and a monitoring method that are obtained can analyze the influence of a joint inclination angle on propagation and attenuation laws of blasting stress waves in the jointed rock mass, and can analyze the influence of different millisecond blasting modes on the stability of an existing tunnel in the jointed rock mass, and can capture a real-time dynamic evolution process of cracks. The stress and strain measurement technologies used can perform omnibearing monitoring and recording for large deformations of surrounding rock under blasting load, and can resist the electromagnetic interference.

14 Claims, 5 Drawing Sheets

(51) Int. Cl.
  *G01N 3/06* (2006.01)
  *G01N 33/24* (2006.01)
  *G01V 20/00* (2024.01)
(52) U.S. Cl.
  CPC ............. *G01N 33/24* (2013.01); *G01V 20/00* (2024.01); *G01N 2203/001* (2013.01); *G01N 2203/003* (2013.01); *G01N 2203/0075* (2013.01); *G01N 2203/0623* (2013.01); *G01N 2203/0641* (2013.01)
(58) Field of Classification Search
  CPC .. G01N 2203/0069; G01N 3/08; G01V 20/00; E21D 9/003
  See application file for complete search history.

(56)     References Cited

FOREIGN PATENT DOCUMENTS

CN    110411871 A  *  11/2019
CN    110554169 A  *  12/2019

OTHER PUBLICATIONS

Jinjin Ge, Ying Xu, "A Method for Making Transparent Hard Rock-Like Material and Its Application", Advances in Materials Science and Engineering, vol. 2019, Article ID 1274171, 14 pages, 2019. https://doi.org/10.1155/2019/1274171 (Year: 2019).*

* cited by examiner

SYSTEM AND METHOD OF MONITORING VIBRATION OF A BLASTING MODEL TEST FOR A JOINTED ROCK MASS

CROSS REFERENCE TO RELATED APPLICATION

This patent application claims the benefit and priority of Chinese Patent Application No. 202011249459.7 filed on Nov. 10, 2020, the disclosure of which is incorporated by reference herein in its entirety as part of the present application.

TECHNICAL FIELD

The present disclosure belongs to the field of blasting theory and technology, and deep rock mechanics, and particularly relates to an improved system and a method of monitoring vibration of a blasting model test for a jointed rock mass.

BACKGROUND ART

Blasting vibration is an important factor that induces dynamic instability of deep-mine tunnels. The researches on the dynamic instability of surrounding rocks of the deep-mine tunnels under the blasting vibration mainly focus on following aspects: the deformation of the surrounding rocks of the tunnels under the blasting vibration, the deterioration of the surrounding rocks of the tunnels during propagation of blasting vibration waves, the influence of a particle vibration velocity on stability of the surrounding rocks, the instable failure of jointed rock masses under vibration conditions, and frequency spectrum analysis. However, there are few researches on the mechanism of action that the blasting vibration induces the dynamic instability of the surrounding rocks of the deep-mine tunnels. Therefore, it is urgent to explore the influence of a joint inclination angle on propagation and attenuation laws of blasting stress waves in the jointed rock masses, and to explore the impacts of blasting load on the stability of existing tunnels in the jointed rock masses and a crack evolution law of surrounding-rock tunnels.

In the specification of the Chinese Patent Application Publication No. CN102175533B, an ultra-large type three-dimensional model test system for geotechnical engineering is published, which includes an ultra-large type model test device, and a hydraulic loading system and a strain displacement test system that are both connected with the ultra-large type model test device. The real-time, automatic and high-precision acquisition and analysis of test results for the tunnel can be realized. However, this device and the method cannot capture and analyze a crack evolution process and a cracking mechanism of the jointed rock mass under blasting load in real time. In a section of "Journal of Rock Mechanics and Engineering" that is Volume 37, 2018, a multifunctional testing machine for geotechnical engineering was introduced, and the propagation and attenuation laws of blasting stress waves in jointed rock masses were studied in virtue of this testing machine. However, test means used in this test can neither monitor both the impact of the blasting stress waves on the stability of existing jointed-surrounding-rock tunnels and the impact of the blasting stress waves on the stability of the jointed rock masses, nor capture and analyze a crack evolution mechanism of the jointed surrounding rock or a crack evolution mechanism of jointed-surrounding-rock tunnels under the blasting load. In a section of "Journal of Rock Mechanics and Engineering" that is Vol. 34, 2015, a simulation test device and a method for the failure mechanism and support technology of a deep-tunnel surrounding rock were introduced. However, this method uses a foil resistance strain gauge which cannot monitor and record large deformations of the surrounding rocks under the blasting load. Furthermore, this method is easily affected by the electromagnetic interference generated by the blasting load. So, test errors are generated, and the method cannot analyze the influence of the joint inclination angle on the propagation and attenuation laws of the blasting stress waves in the jointed rock masses.

It can be seen from the above that, a blasting vibration monitoring system and a method for the existing surrounding rock mass have the following disadvantages.

1) The crack evolution process and the cracking mechanism of the jointed rock mass under the blasting load are not captured and analyzed in real time.

2) The impact of the blasting stress waves on the stability of the existing jointed-surrounding-rock tunnels and the impact of the blasting stress waves on the stability of the jointed rock masses are not monitored.

3) The traditional strain measurement technology cannot monitor and record the large deformations of the surrounding rock under the blasting load, and is easily affected by the electromagnetic interference, thereby resulting in test errors.

4) The omnibearing monitoring and recording for the impact of blasting vibration on the existing tunnels cannot be performed, and the influence of different millisecond blasting modes on the existing tunnels cannot be analyzed.

SUMMARY

In order to solve the above-mentioned problems in the prior art, the present disclosure provides an improved system and a method of monitoring vibration of a blasting model test for a jointed rock mass.

The present disclosure provides an improved system of monitoring vibration of a blasting model test for a jointed rock mass, including: a loading subsystem for three-way load, a model-surface blasting-vibration acquisition subsystem, and a model-interior dynamic stress-strain acquisition subsystem. The loading subsystem for three-way load comprises a reaction frame, a hydraulic jack, a force transfer plate, a three-way pressure control console; the model-surface blasting-vibration acquisition subsystem includes a three-dimensional strain rosette, an ultra-dynamic resistance strain gauge, a dynamic test analyzer, and a blasting vibration monitor; and the model-interior dynamic stress-strain acquisition subsystem includes fiber grating strain sensors, and PVDF piezoelectric pressure sensors.

The three-dimensional strain rosette and the blasting vibration monitor are both arranged on a non-loading surface of a jointed rock mass model 5; the three-dimensional strain rosette is connected with the ultra-dynamic resistance strain gauge via a first circuit; the ultra-dynamic resistance strain gauge is configured to collect and amplify a strain electrical signal generated by the three-dimensional strain rosette 7, and is connected with the dynamic test analyzer via a second circuit. The dynamic test analyzer is configured to display and store the strain electrical signal collected by the ultra-dynamic resistance strain gauge.

The loading subsystem for three-way load applies one-way load, two-way load and three-way load; a maximum load intensity that is applied to a model boundary is 0-100 MPa, which meets requirements of simulating a high ground stress state of a deep-mine tunnel. The reaction frame and the force transfer plate have a sufficient rigidity to meet rigid loading and uniform loading requirements of the jointed rock mass model.

The jointed rock mass model is made of a transparent rock-like material; the jointed rock mass model includes an existing tunnel and blasting holes, and has built-in prefabricated joints with inclination angles α, such as a 30° prefabricated joint, a 60° prefabricated joint, and a 90° prefabricated joint. The prefabricated joints with different inclination angles are simulated by sheet mica; a length of a long axis of each of the prefabricated joints is equal to a thickness of the jointed rock mass; a length of a short axis of each of the prefabricated joints and the thickness of each of the prefabricated joints are selected according to test needs; and each of the inclination angles α of the prefabricated joints is an included angle between a surface of a corresponding one of the prefabricated joints and an axis direction of the jointed rock mass model.

Particularly, the jointed rock mass model has good transparency; the jointed rock mass model monitors a dynamic crack-growth process of the jointed rock mass under blasting load in real time in combination with a high-speed photography; and the jointed rock mass model further analyzes an impact of the blasting load on stability of the existing tunnel.

The fiber grating strain sensors are Bragg fiber grating sensors, the fiber grating strain sensors after being packaged are enabled to maintain sensitive characteristics of bare gates to strain, whereas the fiber grating strain sensors after being packaged are insensitive to or have a negligible range for other non-measurement objects. And transmission fibers used in the fiber grating sensors are enabled to be withstood harsh environments of construction sites, such as casting of a joint model, and vibration of a vibrating rod; and the transmission fibers are enabled to resist electromagnetic interferences under the blasting load.

The PVDF piezoelectric pressure sensors after being packaged are enabled to effectively prevent influence of water on a strain gauge during subsequent pouring of a model test block, and adhesion and matching with a model material are good. Each of the PVDF piezoelectric pressure sensors has a diameter of less than 25 mm and a thickness of less than 10 mm, so as to minimize influence of the PVDF piezoelectric pressure sensor on anisotropy of the model material and ensure authenticity and validity of test data. And each of the PVDF piezoelectric pressure sensors has good mechanical flexibility, thereby effectively avoiding a disadvantage that a traditional strain gauge is not enabled to measure a large deformation.

The fiber grating strain sensors and the PVDF piezoelectric pressure sensors are arranged in any direction on a predetermined section of the jointed rock mass model, and perform omnibearing monitoring, recording and analyzation for a blasting vibration response and a stress-strain relationship of the existing tunnel.

An optical signal collected by the fiber grating strain sensors is converted into an electric signal after being demodulated by a high-speed demodulation system; the electric signal is adjusted by an adjustment system and transmitted to a display for recording and storage. And the PVDF piezoelectric pressure sensors are connected with a voltage amplifier via a third circuit; and the voltage amplifier is connected with the display via a fourth circuit to display and record a piezoelectric signal.

The blasting holes are arranged in a tunnel face of the existing tunnel, and an impact of blasting vibration generated by millisecond blasting on the existing tunnel is analyzed, so as to optimize blasting parameters and provide support for safe and efficient blasting and tunneling.

Preferably, the blasting holes comprise five blasting holes, four millisecond blasting modes are comprised: first, the five blasting holes are simultaneously detonated; second, middle ones of the blasting holes are detonated first, and after a predetermined tine interval, surrounding four of the blasting holes are detonated simultaneously; third, the middle ones of the blasting holes are only detonated; and fourth, the surrounding four of the blasting holes 9 are only detonated simultaneously.

An improved method for monitoring blasting vibration of a jointed rock mass, wherein the method comprises following steps.

In step one, determination of relevant dimensions of a jointed rock mass model: enabling an existing tunnel of the jointed rock mass model to be a circular cavity commonly used in deep underground engineering; determining an excavation diameter $\Phi_1$ and a tunneling depth $d_1$ of the existing tunnel 6 according to a similar theory and a size of the jointed rock mass model; determining a diameter $\Phi_2$ and a depth $d_2$ of each of blasting holes 9; fixing sheet mica with different angles in a mold according to test needs; and pouring a first layer of transparent rock-like material, wherein a pouring thickness is equal to a difference value among a thickness d of the mold, the tunneling depth $d_1$ and the depth $d_2$ of each of the blasting holes.

In step two, reservation of the blasting holes: presetting seamless steel pipes at a center of a surface of the first layer of transparent rock-like material to reserve the blasting holes, after the first layer of transparent rock-like material is stand and harden; wherein an inner diameter and a height of each of the seamless steel pipes that are preset have a same diameter and a same depth as the diameter $\Phi_2$ and the depth $d_2$ of a corresponding one of the blasting holes, respectively.

In step three, pouring of a second layer of transparent rock-like material: enabling a pouring thickness of the second layer of transparent rock-like material to be 0.5 times the depth $d_2$ of each of the blasting holes; before the second layer of transparent rock-like material is completely hardened, rotating the seamless steel pipes configured to reserve the blasting holes, so as to prevent the seamless steel pipes from bonding to the second layer of transparent rock-like material and being difficult to be pulled away.

In step four, embedding of stress and strain sensors for the jointed rock mass: arranging strain measuring lines and stress measuring lines on a surface of the second layer of transparent rock-like material along any direction (e.g., an axis direction, a diagonal direction and so on) of the jointed rock mass model, after the second layer of transparent rock-like material is completely hardened; wherein the strain measuring lines are formed by a plurality of strain measuring points; enabling each of strain measuring points to adhere a fiber grating strain sensor; similarly, wherein the stress measuring lines are formed by a plurality of several stress measuring points, enabling each of the stress measuring points to adhere a PVDF piezoelectric pressure sensor; and enabling the stress measuring points and the strain measuring points to be arranged on two sides of a joint according to test requirements, so as to measure an impact of blasting load on the jointed rock mass.

In step five, roughening of layered surfaces: enabling a surface of a model material is raked by using an iron rake to obtain a rough surface with a thickness of about 5 mm, after the stress measuring points and the strain measuring points are embedded, thereby reducing layering caused by layered pouring, so that the model material after being undergone layered pouring are closely bonded with each other to improve integrity of a model test block.

In step six, pouring of a third layer of transparent rock-like material: enabling a pouring thickness of the third layer of transparent rock-like material to be 0.5 times the depth $d_2$ of each of the blasting holes; rotating the seamless steel pipes configured to reserve the blasting holes again, before the third layer of transparent rock-like material is completely hardened, so as to prevent the seamless steel pipes from bonding to the third layer of transparent rock-like material and being difficult to be pulled away; and after the third layer of transparent rock-like material is completely hardened, pulling away the seamless steel pipes that are preset; and finishing the reservation of the blasting holes at this moment.

In step seven, prefabrication of the existing tunnel: presetting the seamless steel pipes at a center of a surface of the third layer of transparent rock-like material, after the third layer of transparent rock-like material is completely hardened, so as to prefabricate the existing tunnel; enabling the seamless steel pipes that are preset to each have a same inner diameter and a same height as the excavation diameter $\Phi_1$ and the depth $d_1$ of the existing tunnel; repeating the step three and step six to complete the prefabrication of the existing tunnel, and arrangement of the stress measuring points and the strain measuring points around the existing tunnel; wherein the stress measuring points and the strain measuring points are reasonably arranged according to the test requirements and joint positions.

In step eight, implementation of blasting: adding a high-strength transparent glass cover outside the jointed rock mass model; setting up high-speed camera equipment at a predetermined distance from an outer surface of the glass cover, so as to capture a dynamic crack-growth process in real time; applying the blasting load and performing model blasting, after setting up; and collecting relevant data to analyze influence of a joint inclination angle on propagation and attenuation laws of blasting stress waves in the jointed rock mass, and to analyze an impact of the blasting load on stability of the existing tunnel in the jointed rock mass.

A blasting model for a transparent jointed rock mass in the above improved system of monitoring vibration of a blasting model test for a jointed rock mass, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

The present disclosure provides an improved system and a method of monitoring vibration of a blasting model test for a jointed rock mass. A transparent jointed rock mass blasting model and a monitoring method that are obtained can be used to analyze the influence of a joint inclination angle on propagation and attenuation laws of blasting stress waves in a jointed rock mass, to analyze the influence of different millisecond blasting modes on the stability of an existing tunnel in the jointed rock mass, and to capture a dynamic crack-evolution process in real time. The stress and strain measurement technologies used can perform the omnibearing monitoring and recording for large deformations of surrounding rock under blasting load, and can resist the electromagnetic interference, thereby making the test data more reliable and truer.

Other features and advantages of the present disclosure will be described in detail in the following description of the embodiments.

BRIEF DESCRIPTION OF THE DRAWINGS

The accompanying drawings constituting a part of the present disclosure are used to provide a further understanding of the present disclosure, and the exemplary embodiments of the present disclosure and descriptions thereof are used to explain the present disclosure, and do not constitute an improper limit to the present disclosure.

Figure 1:
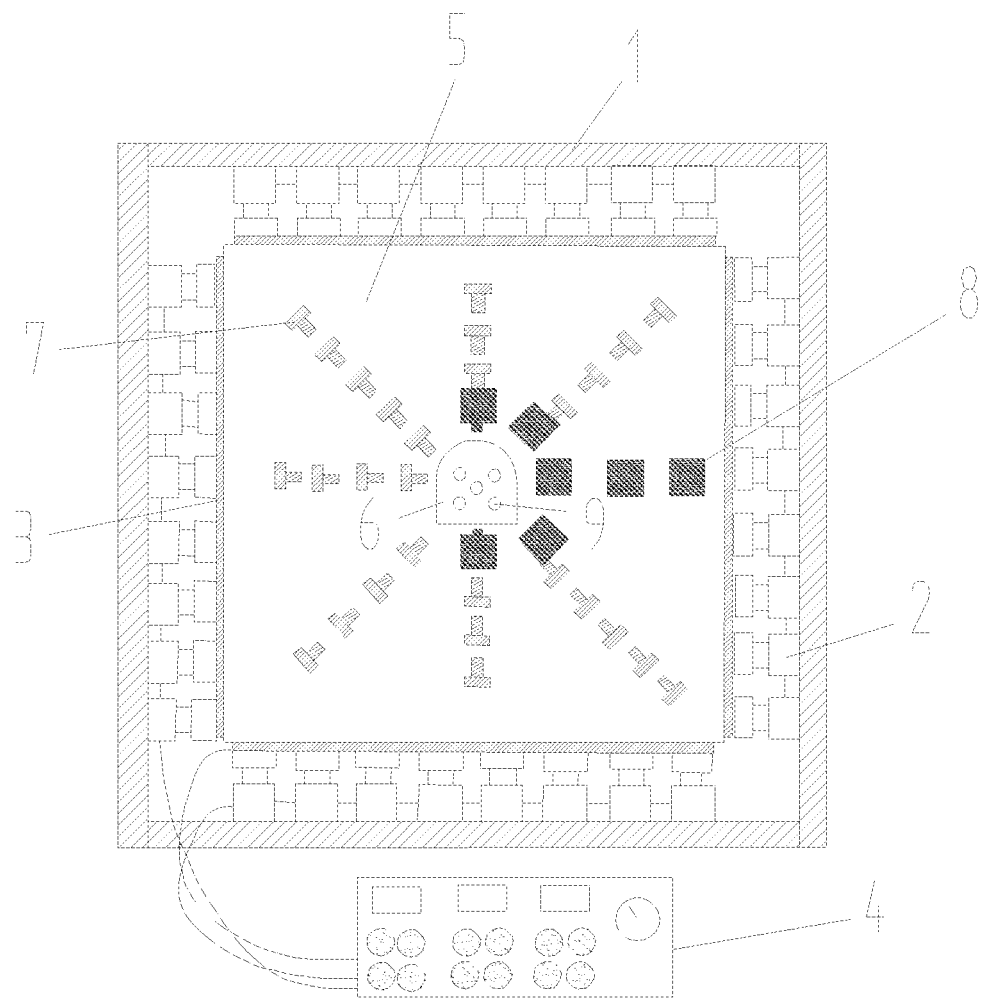
FIG. 1 is a schematic diagram of an improved three-dimensional blasting model test device for a deep high-stress tunnel.

Reference signs in drawings: 1—reaction frame, 2—hydraulic jack, 3—force transfer plate, 4—three-way pressure control console, 5—jointed rock mass model, 6—existing tunnel, 7—three-dimensional strain rosette, 8—blasting vibration monitor, 9—blasting hole, 10—30° prefabricated joint, 11—60° prefabricated joint, 12—90° prefabricated joint, 13—fiber grating strain sensor, and 14—PVDF piezoelectric pressure sensor.

DETAILED DESCRIPTION OF THE EMBODIMENTS

The present disclosure will be further described below in conjunction with the drawings.

In order to make the objectives, technical solutions and advantages of the present disclosure clearer, the embodiments of the present disclosure will be described in further detail below in conjunction with the drawings. It should be understood that the specific embodiments described here are merely used to illustrate and explain the present disclosure, and are not used to limit the present disclosure.

In the description of the present disclosure, it should be noted that the orientation or positional relationship indicated by the terms "center," "upper," "lower," "left," "right," "vertical," "horizontal," "inner," "outer," and the like are based on the orientation or positional relationship shown in the drawings, only used for describing the present disclosure and simplifying the description, instead of indicating or implying that a device or an element specified must have a specific orientation, be constructed and operated in a specific orientation, and therefore cannot be understood as a limit to the present disclosure. In addition, the terms "first," "second," and "third" are only used for the purpose of description, and cannot be understood as indicating or implying relative importance.

In the description of the present disclosure, it should be noted that, unless otherwise specified and limited expressly, the terms "mount," "link," and "connect" should be understood in a broad sense. For example, it may be a fixed connection, or a detachable connection, or an integral connection; it may also be a direct like or an indirect link with an intermediate medium; and it may still be internal communication between two elements. For a person of ordinary skill in the art, the specific meanings of the above-mentioned terms in the present disclosure can be understood in specific situations.

Figure 2:
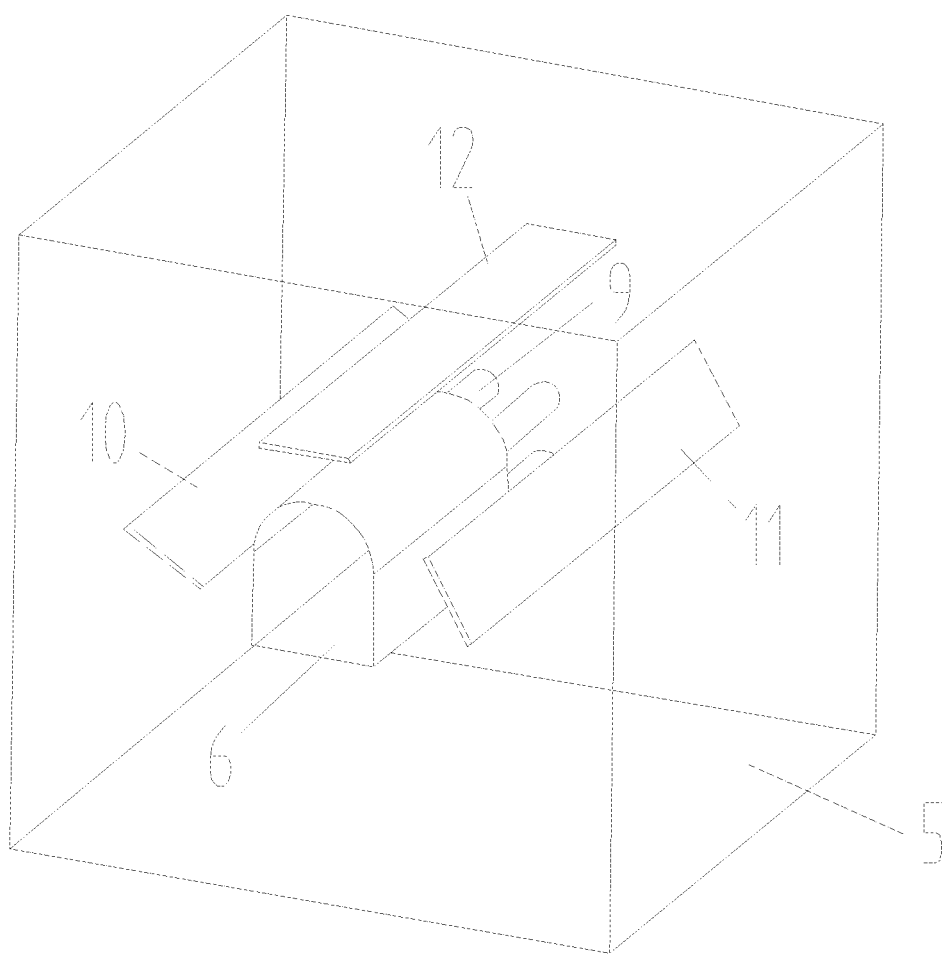
FIG. 2 is a schematic diagram of joint distribution and blasting holes in rock mass.
Figure 3:
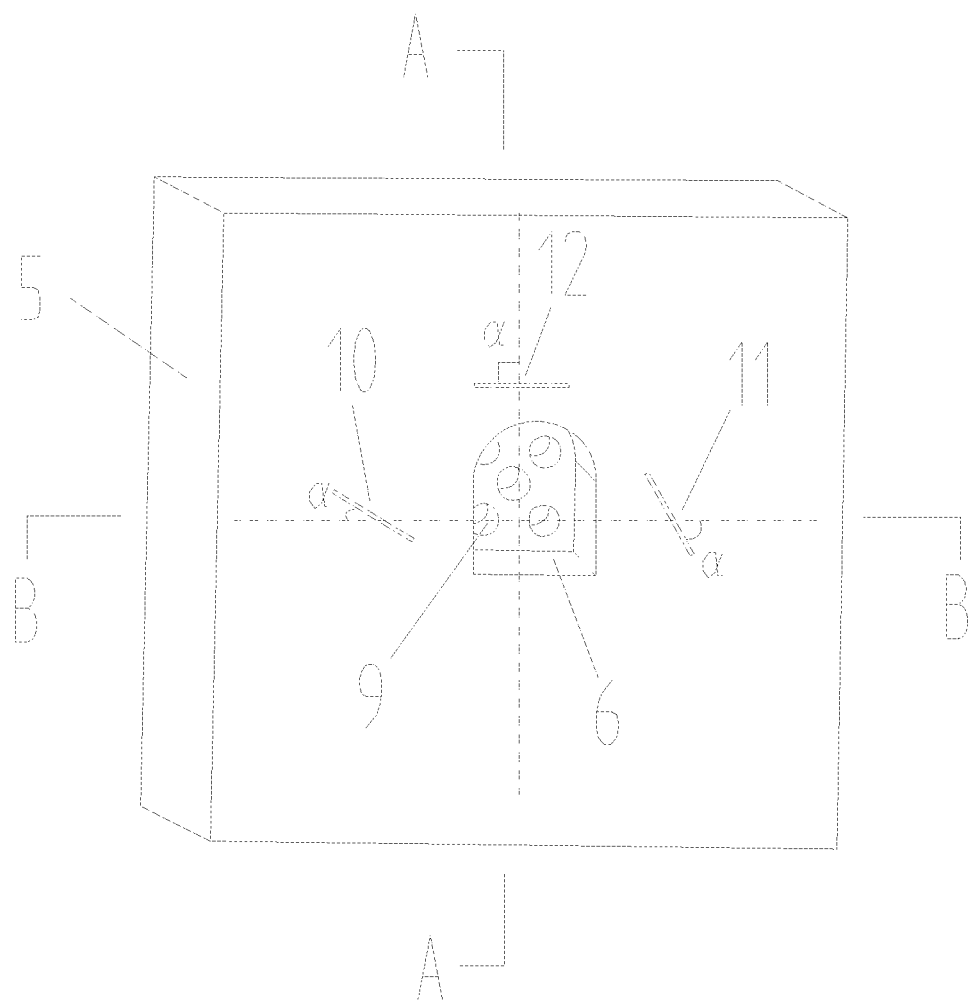
FIG. 3 is a schematic diagram of a jointed-surrounding-rock tunnel.
Figure 4:
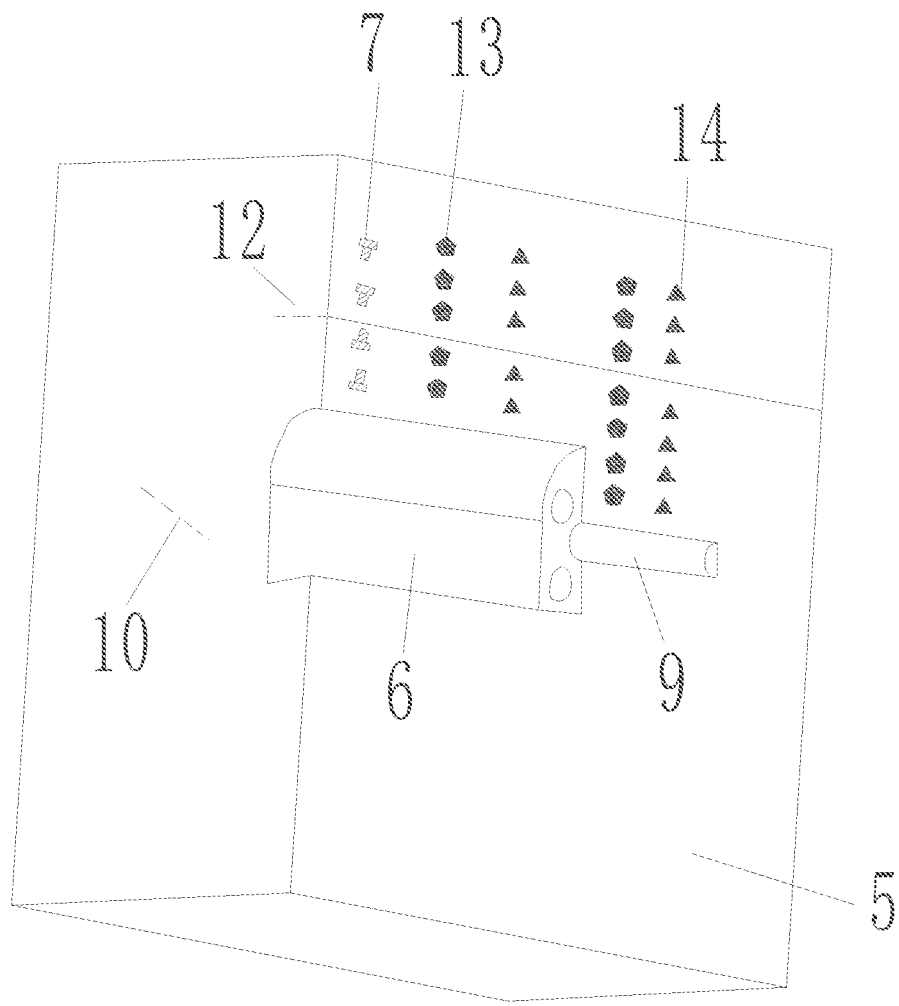
FIG. 4 is a sectional view taken along line A-A of FIG. 3.
Figure 5:
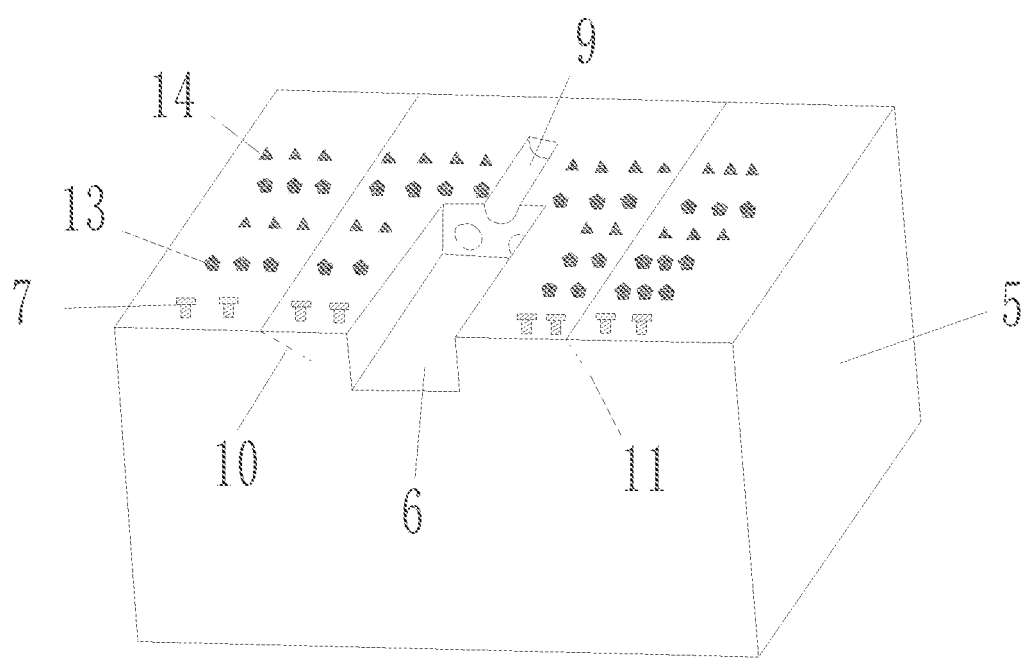
FIG. 5 is a sectional view taken along line B-B of FIG. 3.

As shown in FIG. 1 to FIG. 5, a preferred embodiment of the present disclosure provides an improved system and a method of monitoring vibration of a blasting model test for a jointed rock mass as follows.

In a first embodiment, an improved system of monitoring vibration of a blasting model test for a jointed rock mass includes: a loading subsystem for three-way load, a model-surface blasting-vibration acquisition subsystem, and a model-interior dynamic stress-strain acquisition subsystem. The loading subsystem for three-way load includes a reaction frame 1, a hydraulic jack 2, a force transfer plate 3, and a three-way pressure control console 4. The model-surface blasting-vibration acquisition subsystem includes a three-dimensional strain rosette 7, an ultra-dynamic resistance strain gauge, a dynamic test analyzer, and a blasting vibration monitor 8. The model-interior dynamic stress-strain acquisition subsystem includes fiber grating strain sensors 13, and PVDF (Polyvinylidene fluoride) piezoelectric pressure sensors 14.

The three-dimensional strain rosette 7 and the blasting vibration monitor 8 are both arranged on a non-loading surface of a jointed rock mass model 5. The three-dimensional strain rosette 7 is connected with the ultra-dynamic resistance strain gauge via a circuit. The ultra-dynamic resistance strain gauge is configured to collect and amplify a strain electrical signal generated by the three-dimensional strain rosette 7, and is connected with the dynamic test analyzer via a circuit. The dynamic test analyzer is configured to display and store the strain electrical signal collected by the ultra-dynamic resistance strain gauge.

The loading subsystem for three-way load can apply one-way load, two-way load and three-way load. A maximum load intensity that is applied to a model boundary is 0-100 MPa, which meets the requirements of simulating a high ground stress state of a deep mine tunnel. The reaction frame 1 and the force transfer plate 3 have a sufficient rigidity to meet rigid loading and uniform loading requirements of the jointed rock mass model 5.

The jointed rock mass model 5 is made of a transparent rock-like material. The jointed rock mass model 5 includes an existing tunnel 6 and blasting holes 9. The jointed rock mass model 5 has built-in prefabricated joints with inclination angles α, such as a 30° prefabricated joint 10, a 60° prefabricated joint 11, and a 90° prefabricated joint 12. The prefabricated joints with different inclination angles are simulated by sheet mica. A length of a long axis of the prefabricated joint is equal to a thickness of the jointed rock mass. A length of a short axis of the prefabricated joint and a thickness of the jointed rock mass can be selected according to test needs. The inclination angle α of the prefabricated joint is an included angle between a surface of this prefabricated joint and an axis direction of the jointed rock mass model 5.

In particular, the jointed rock mass model 5 has good transparency. The jointed rock mass model 5 can monitor a dynamic crack-growth process of the jointed rock mass under blasting load in real time in combination with a high-speed photography. The jointed rock mass model 5 can further analyze the impact of the blasting load on the stability of the existing tunnel 6.

The fiber grating strain sensors 13 are fiber grating sensors. The fiber grating strain sensors 13 after being packaged need to maintain sensitive characteristics of a bare gate to strain, whereas the fiber grating strain sensors 13 after being packaged are insensitive to or have a negligible range for other non-measurement objects. Transmission fibers used in the fiber grating sensors 13 can withstand harsh environments of construction sites, such as casting of the joint model, and vibration of a vibrating rod. Transmission fibers can resist the electromagnetic interference under the blasting load.

The PVDF piezoelectric pressure sensor 14 after being packaged can effectively present the influence of water on a strain gauge during subsequent pouring of a model test block, thereby realizing good adhesion and matching with the model material. Each of the PVDF piezoelectric pressure sensors 14 should have a diameter of less than 25 mm and a thickness of less than 10 mm, so as to minimize the influence of the PVDF piezoelectric pressure sensors 14 on the anisotropy of a model material and ensure the authenticity and validity of test data. The PVDF piezoelectric pressure sensors 14 have good mechanical flexibility, and can effectively avoid the disadvantage that a traditional strain gauge cannot measure a large deformation.

The fiber grating strain sensors 13 and the PVDF piezoelectric pressure sensors 14 can be arranged in any direction on a predetermined section of the jointed rock mass model, and can perform omnibearing monitoring, recording and analyzation for a blasting vibration response and a stress-strain relationship of the existing tunnel 6.

An optical signal collected by the fiber grating strain sensors 13 is demodulated by a high-speed demodulation system and is converted into an electric signal. The electric signal is adjusted by an adjustment system and transmitted to a display for recording and storage. The PVDF piezoelectric pressure sensors 14 are connected with a voltage amplifier via a circuit. The voltage amplifier is connected with the display via a circuit to display and record a piezoelectric signal.

A plurality of the blasting holes 9 may be arranged in a tunnel face of the existing tunnel. The impact of blasting vibration generated by millisecond blasting on the existing tunnel 6 can be analyzed, so as to optimize blasting parameters and provide support for safe and efficient blasting and tunneling.

Preferably, five blasting holes 9 may be arranged, and the arrangement thereof is shown in the figure. Four millisecond blasting modes can be included: first, the five blasting holes 9 are simultaneously detonated; second, the blasting holes 9 in the middle are detonated first, and after a predetermined time interval, the surrounding four blasting holes 9 are detonated at the same time; third, only the blasting holes 9 in the middle are detonated; and fourth, only the surrounding four blasting holes 9 are detonated at the same time.

In a second embodiment, the method for monitoring blasting vibration of a jointed rock mass includes the following steps one to eight.

In step one, determination of relevant dimensions of a jointed rock mass model: an existing tunnel of the jointed rock mass model is enabled to be a circular cavity commonly used in deep underground engineering; an excavation diameter $\Phi_1$ and a tunneling depth $d_1$ of the existing tunnel 6 are determined according to a similar theory and a size of the jointed rock mass model; a diameter $\Phi_2$ and a depth $d_2$ of each of blasting holes 9 are determined; sheet mica with different angles is fixed in a mold according to test needs; and a first layer of transparent rock-like material is poured, where a pouring thickness is equal to a difference value among a thickness d of the mold, the tunneling depth $d_1$ and the depth $d_2$ of each of the blasting holes.

In step two, reservation of the blasting holes: seamless steel pipes are preset at a center of a surface of the first layer of transparent rock-like material to reserve the blasting holes, after the first layer of transparent rock-like material is stand and harden; where an inner diameter and a height of each of the seamless steel pipes that are preset have a same diameter and a same depth as the diameter $\Phi_2$ and the depth $d_2$ of a corresponding one of the blasting holes 9, respectively.

In step three, pouring of a second layer of transparent rock-like material: a pouring thickness of the second layer of transparent rock-like material is enabled to be 0.5 times the depth $d_2$ of each of the blasting holes; before the second layer of transparent rock-like material is completely hardened, the seamless steel pipes configured to reserve the blasting holes are rotated, so as to prevent the seamless steel pipes from bonding to the second layer of transparent rock-like material and being difficult to be pulled away.

In step four, embedding of stress and strain sensors for the jointed rock mass: strain measuring lines and stress measuring lines are arranged on a surface of the second layer of transparent rock-like material along any direction (an axis direction, a diagonal direction and so on) of the jointed rock mass model, after the second layer of transparent rock-like material is completely hardened; where the strain measuring lines are formed by a plurality of strain measuring points; each of strain measuring points is enabled to adhere a fiber grating strain sensor 13; similarly, the stress measuring lines are formed by a plurality of several stress measuring points; each of the stress measuring points is enabled to adhere a PVDF piezoelectric pressure sensor 14; and the stress measuring points and the strain measuring points are enabled to be arranged on two sides of a joint according to test requirements, so as to measure an impact of blasting load on the jointed rock mass.

In step five, roughening of layered surfaces: a surface of a model material is raked by using an iron rake is enabled to obtain a rough surface with a thickness of about 5 mm, after the stress measuring points and the strain measuring points are embedded, thereby reducing layering caused by layered pouring, so that the model material after being undergone layered pouring are closely bonded with each other to improve integrity of a model test block.

In step six, pouring of a third layer of transparent rock-like material: a pouring thickness of the third layer of transparent rock-like material is enabled to be 0.5 times the depth $d_2$ of each of the blasting holes; the seamless steel pipes configured to reserve the blasting holes are rotated again, before the third layer of transparent rock-like material is completely hardened, so as to prevent the seamless steel pipes from bonding to the third layer of transparent rock-like material and being difficult to be pulled away; and after the third layer of transparent rock-like material is completely hardened, the seamless steel pipes that are preset are pulled away; and the reservation of the blasting holes at this moment is finished.

In step seven, prefabrication of the existing tunnel: the seamless steel pipes are preset at a center of a surface of the third layer of transparent rock-like material, after the third layer of transparent rock-like material is completely hardened, so as to prefabricate the existing tunnel; the seamless steel pipes that are preset are enabled to each have a same inner diameter and a same height as the excavation diameter $\Phi_1$ and the depth $d_1$ of the existing tunnel, respectively; the step three and step six are repeated to complete the prefabrication of the existing tunnel, and arrangement of the stress measuring points and the strain measuring points around the existing tunnel; where the stress measuring points and the strain measuring points are reasonably arranged according to the test requirements and joint positions.

In step eight, implementation of blasting three-way load is applied and stabilizing pressure is stabilized according to a test scheme; a high-strength transparent glass cover is added outside the jointed rock mass model, after the three-way load is applied; high-speed camera equipment is set up at a predetermined distance from an outer surface of the glass cover, so as to capture a dynamic crack-growth process in real time; the blasting load and performing model blasting are applied, after setting up; and relevant data is collected to analyze influence of a joint inclination angle on propagation and attenuation laws of blasting stress waves in the jointed rock mass, and to analyze an impact of the blasting load on stability of the existing tunnel in the jointed rock mass.

According to the above content, the present disclosure provides an improved system and a method of monitoring vibration of a blasting model test for a jointed rock mass. A transparent blasting model for a jointed rock mass and a monitoring method that are obtained can be used to analyze the impact of the joint inclination angle on the propagation and attenuation laws of the blasting stress waves in the jointed rock mass, and the influence of different millisecond blasting modes on the stability of the existing tunnel in the jointed rock mass, and to capture a dynamic evolution process of cracks in real time. The stress and strain measurement technologies that are used can perform omnibearing monitoring and recording of large deformations of surrounding rock under the blasting load, and can resist the electromagnetic interference, thereby making the test data more reliable and truer.

It can be known from technical knowledge that the present disclosure can be implemented by other implementations that do not deviate from its spirit or essential features. Therefore, the implementations disclosed above are merely illustrative in all aspects, and not exclusive. All changes within the scope of the present disclosure or within the scope equivalent to the present disclosure are included in the present disclosure.

What is claimed is:

1. A system of monitoring vibration of a blasting model test for a jointed rock mass, the system comprising: a loading subsystem for three-way load, a model-surface blasting-vibration acquisition subsystem, and a model-interior dynamic stress-strain acquisition subsystem; wherein the loading subsystem for three-way load comprises a reaction frame, a hydraulic jack, a force transfer plate, a three-way pressure control console; the model-surface blasting-vibration acquisition subsystem comprises a three-dimensional strain rosette, an ultra-dynamic resistance strain gauge, a dynamic test analyzer, and a blasting vibration monitor; and the model-interior dynamic stress-strain acquisition subsystem comprises fiber grating strain sensors, and PVDF piezoelectric pressure sensors;

the three-dimensional strain rosette and the blasting vibration monitor are both arranged on a non-loading surface of a jointed rock mass model; the three-dimensional strain rosette is connected with the ultra-dynamic resistance strain gauge via a first circuit; the ultra-dynamic resistance strain gauge is configured to collect and amplify a strain electrical signal generated by the three-dimensional strain rosette, and is connected with the dynamic test analyzer via a second circuit; and the dynamic test analyzer is configured to display and store the strain electrical signal collected by the ultra-dynamic resistance strain gauge.

2. The system of monitoring vibration of a blasting model test for a jointed rock mass according to claim 1, wherein the loading subsystem for three-way load applies one-way load, two-way load and three-way load; a maximum load intensity that is applied to a model boundary is 0-100 MPa, which meets requirements of simulating a high ground stress state of a deep-mine tunnel; and the reaction frame and the force transfer plate have a sufficient rigidity to meet rigid loading and uniform loading requirements of the jointed rock mass model.

3. A blasting model for a transparent jointed rock mass in the system of monitoring vibration of a blasting model test for a jointed rock mass according to claim 2, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

4. The system of monitoring vibration of a blasting model test for a jointed rock mass according to claim 1, wherein
the jointed rock mass model is made of a transparent rock-like material; the jointed rock mass model comprises an existing tunnel and blasting holes, and has built-in prefabricated joints with inclination angles α, such as a 30° prefabricated joint, a 60° prefabricated joint, and a 90° prefabricated joint; the prefabricated joints with different inclination angles are simulated by sheet mica; a length of a long axis of each of the prefabricated joints is equal to a thickness of the jointed rock mass; a length of a short axis of each of the prefabricated joints and the thickness of each of the prefabricated joints are selected according to test needs; and each of the inclination angles α of the prefabricated joints is an included angle between a surface of a corresponding one of the prefabricated joints and an axis direction of the jointed rock mass model; and
particularly, the jointed rock mass model has good transparency; the jointed rock mass model monitors a dynamic crack-growth process of the jointed rock mass under blasting load in real time in combination with a high-speed photography; and the jointed rock mass model further analyzes an impact of the blasting load on stability of the existing tunnel.

5. A blasting model for a transparent jointed rock mass in the system of monitoring vibration of a blasting model test for a jointed rock mass according to claim 4, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

6. The system of monitoring vibration of a blasting model test for a jointed rock mass according to claim 1, wherein
the fiber grating strain sensors are fiber grating sensors, the fiber grating strain sensors after being packaged are enabled to maintain sensitive characteristics of bare gates to strain, whereas the fiber grating strain sensors after being packaged are insensitive to or have a negligible range for other non-measurement objects; and transmission fibers used in the fiber grating sensors are enabled to be withstood harsh environments of construction sites, such as casting of a joint model, and vibration of a vibrating rod; and the transmission fibers are enabled to resist electromagnetic interferences under the blasting load;
the PVDF piezoelectric pressure sensors after being packaged are enabled to effectively prevent influence of water on a strain gauge during subsequent pouring of a model test block, and adhesion and matching with a model material are good; each of the PVDF piezoelectric pressure sensors has a diameter of less than 25 mm and a thickness of less than 10 mm, so as to minimize influence of the PVDF piezoelectric pressure sensor on anisotropy of the model material and ensure authenticity and validity of test data; and each of the PVDF piezoelectric pressure sensors has good mechanical flexibility, thereby effectively avoiding a disadvantage that a traditional strain gauge is not enabled to measure a large deformation.

7. A blasting model for a transparent jointed rock mass in the system of monitoring vibration of a blasting model test for a jointed rock mass according to claim 6, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

8. The system of monitoring vibration of a blasting model test for a jointed rock mass according to claim 1, wherein
the fiber grating strain sensors and the PVDF piezoelectric pressure sensors are arranged in any direction on a predetermined section of the jointed rock mass model, and perform omnibearing monitoring, recording and analyzation for a blasting vibration response and a stress-strain relationship of the existing tunnel.

9. A blasting model for a transparent jointed rock mass in the system of monitoring vibration of a blasting model test for a jointed rock mass according to claim 8, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

10. The system of monitoring vibration of a blasting model test for a jointed rock mass according to claim 1, wherein
an optical signal collected by the fiber grating strain sensors is converted into an electric signal after being demodulated by a high-speed demodulation system; the electric signal is adjusted by an adjustment system and transmitted to a display for recording and storage; and the PVDF piezoelectric pressure sensors are connected with a voltage amplifier via a third circuit; and the voltage amplifier is connected with the display via a fourth circuit to display and record a piezoelectric signal.

11. A blasting model for a transparent jointed rock mass in the system of monitoring vibration of a blasting model test for a jointed rock mass according to claim 10, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

12. The system of monitoring vibration of a blasting model test for a jointed rock mass according to claim 1, wherein
the blasting holes are arranged in a tunnel face of the existing tunnel, and an impact of blasting vibration generated by millisecond blasting on the existing tunnel is analyzed, so as to optimize blasting parameters and provide support for safe and efficient blasting and tunneling;
preferably, the blasting holes comprise five blasting holes; four millisecond blasting modes are comprised: first, the five blasting holes are simultaneously detonated; second, middle ones of the blasting holes are detonated first, and after a predetermined tine interval, surrounding four of the blasting holes are detonated simultaneously; third, the middle ones of the blasting holes are only detonated; and fourth, the surrounding four of the blasting holes are only detonated simultaneously.

13. A blasting model for a transparent jointed rock mass in the system of monitoring vibration of a blasting model test for a jointed rock mass according to claim 1, wherein the blasting model for a transparent jointed rock mass is configured to analyze influence of a joint inclination angle on propagation and attenuation laws of blasting stress waves in the jointed rock mass, to analyze impact of blasting load on stability of an existing tunnel in the jointed rock mass, and to capture a dynamic crack-evolution process in real time.

14. A method for monitoring blasting vibration of a jointed rock mass, wherein the method comprises:

step one, determination of relevant dimensions of a jointed rock mass model: enabling an existing tunnel of the jointed rock mass model to be a circular cavity commonly used in deep underground engineering; determining an excavation diameter and a tunneling depth of the existing tunnel according to a similar theory and a size of the jointed rock mass model; determining a diameter and a depth of each of blasting holes; fixing sheet mica with different angles in a mold according to test needs; and pouring a first layer of transparent rock-like material, wherein a pouring thickness is equal to a difference value among a thickness d of the mold, the tunneling depth and the depth of each of the blasting holes;

step two, reservation of the blasting holes: presetting seamless steel pipes at a center of a surface of the first layer of transparent rock-like material to reserve the blasting holes, after the first layer of transparent rock-like material is stand and harden; wherein an inner diameter and a height of each of the seamless steel pipes that are preset have a same diameter and a same depth as the diameter and the depth of a corresponding one of the blasting holes, respectively;

step three, pouring of a second layer of transparent rock-like material: enabling a pouring thickness of the second layer of transparent rock-like material to be 0.5 times the depth of each of the blasting holes; before the second layer of transparent rock-like material is completely hardened, rotating the seamless steel pipes configured to reserve the blasting holes, so as to prevent the seamless steel pipes from bonding to the second layer of transparent rock-like material and being difficult to be pulled away;

step four, embedding of stress and strain sensors for the jointed rock mass: arranging strain measuring lines and stress measuring lines on a surface of the second layer of transparent rock-like material along an axis direction of the jointed rock mass model, after the second layer of transparent rock-like material is completely hardened; wherein the strain measuring lines are formed by a plurality of strain measuring points; enabling each of strain measuring points to adhere a fiber grating strain sensor; similarly, wherein the stress measuring lines are formed by a plurality of several stress measuring points, enabling each of the stress measuring points to adhere a PVDF piezoelectric pressure sensor; and enabling the stress measuring points and the strain measuring points to be arranged on two sides of a joint according to test requirements, so as to measure an impact of blasting load on the jointed rock mass;

step five, roughening of layered surfaces: enabling a surface of a model material is raked by using an iron rake to obtain a rough surface with a thickness of about 5 mm, after the stress measuring points and the strain measuring points are embedded, thereby reducing layering caused by layered pouring, so that the model material after being undergone layered pouring are closely bonded with each other to improve integrity of a model test block;

step six, pouring of a third layer of transparent rock-like material: enabling a pouring thickness of the third layer of transparent rock-like material to be 0.5 times the depth of each of the blasting holes; rotating the seamless steel pipes configured to reserve the blasting holes again, before the third layer of transparent rock-like material is completely hardened, so as to prevent the seamless steel pipes from bonding to the third layer of transparent rock-like material and being difficult to be pulled away; and after the third layer of transparent rock-like material is completely hardened, pulling away the seamless steel pipes that are preset; and finishing the reservation of the blasting holes at this moment;

step seven, prefabrication of the existing tunnel: presetting the seamless steel pipes at a center of a surface of the third layer of transparent rock-like material, after the third layer of transparent rock-like material is completely hardened, so as to prefabricate the existing tunnel; enabling the seamless steel pipes that are preset to each have a same inner diameter and a same height as the excavation diameter and the depth of the existing tunnel, respectively; repeating the step three and step six to complete the prefabrication of the existing tunnel, and arrangement of the stress measuring points and the strain measuring points around the existing tunnel; wherein the stress measuring points and the strain measuring points are reasonably arranged according to the test requirements and joint positions; and step eight, implementation of blasting: applying three-way load and stabilizing pressure according to a test scheme; adding a high-strength transparent glass cover outside the jointed rock mass model, after the three-way load is applied; setting up high-speed camera equipment at a predetermined distance from an outer surface of the glass cover, so as to capture a dynamic crack-growth process in real time; applying the blasting load and performing model blasting, after setting up; and collecting relevant data to analyze influence of a joint inclination angle on propagation and attenuation laws of blasting stress waves in the jointed rock mass, and to analyze an impact of the blasting load on stability of the existing tunnel in the jointed rock mass.

* * * * *